US00PP27111P2

(12) United States Plant Patent
Meinl

(10) Patent No.: US PP27,111 P2
(45) Date of Patent: Aug. 30, 2016

(54) ***HYDRANGEA* PLANT NAMED 'HORKRON'**

(50) Latin Name: *Hydrangea macrophylla*
Varietal Denomination: Horkron

(71) Applicant: Katrin Meinl, Dresden (DE)

(72) Inventor: Katrin Meinl, Dresden (DE)

(73) Assignee: Kühne Jungpflanzen Claus & Torsten Kühne Gbr, Dresden (DE)

( * ) Notice: Subject to any disclaimer, the term of this patent is extended or adjusted under 35 U.S.C. 154(b) by 86 days.

(21) Appl. No.: 14/120,668

(22) Filed: Jun. 14, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

UPOV hit for *Hydrangea macrophylla* named 'Horkron', QZ PBR 35712, publication date Oct. 15, 2010.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'Horkron', characterized by its compact, upright and mounded plant habit; moderately vigorous growth habit; strong stems; and large mophead-type inflorescences with large pink-colored sterile flowers.

2 Drawing Sheets

Botanical designation: *Hydrangea macrophylla.*
Cultivar denomination: 'HORKRON'.

BACKGROUND OF THE INVENTION

The present invention relates to a new and distinct cultivar of *Hydrangea* plant, botanically known as *Hydrangea macrophylla* and hereinafter referred to by the name 'Horkron'.

The new *Hydrangea* plant is a product of a planned breeding program conducted by the Inventor in Dresden, Germany. The objective of the breeding program was to develop new container-type *Hydrangea* plants with strong stems and attractive leaf, stem and flower coloration.

The new *Hydrangea* plant originated from a cross-pollination in 2002 of a proprietary selection of *Hydrangea macrophylla* identified as code number 13-88/2, not patented, as the female, or seed parent and a proprietary selection of *Hydrangea macrophylla* identified as code number 6-97/2, not patented, as the male, or pollen, parent. The new *Hydrangea* plant was discovered and selected by the Inventor in 2004 as a flowering plant within the progeny of the stated cross-pollination in a controlled environment in Dresden, Germany.

Asexual reproduction of the new cultivar by softwood cuttings in Dresden, Germany since June, 2004 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Horkron'. These characteristics in combination distinguish 'Horkron' as a new and distinct *Hydrangea* plant:

1. Compact, upright and mounded plant habit.
2. Moderately vigorous growth habit.
3. Strong stems.
4. Large mophead-type inflorescences with large pink-colored sterile flowers.

Plants of the new *Hydrangea* differ primarily from plants of the female parent selection in the following characteristics:

1. Plants of the new *Hydrangea* have more compact than and not as vigorous as plants of the female parent selection.
2. Plants of the new *Hydrangea* are more freely branching than plants of the female parent selection.
3. Leaves of plants of the new *Hydrangea* are darker green in color than leaves of plants of the female parent selection.

Plants of the new *Hydrangea* differ primarily from plants of the male parent selection in the following characteristics:

1. Plants of the new *Hydrangea* are more compact than and not vigorous as plants of the male parent selection.
2. Plants of the new *Hydrangea* flower earlier than plants of the male parent selection.
3. Plants of the new *Hydrangea* have larger inflorescences than plants of the male parent selection.
4. Plants of the new *Hydrangea* and the male parent selection differ in flower color as plants of the male parent selection have dark pink-colored flowers.

Plants of the new *Hydrangea* can be compared to plants of *Hydrangea macrophylla* 'Horsonn', disclosed in U.S. Plant Pat. No. 19,802. Plants of the new *Hydrangea* differ primarily from plants of 'Horsonn' in the following characteristics:

1. Plants of the new *Hydrangea* are more compact than and not as vigorous as plants of 'Horsonn'.

2. Leaves of plants of the new *Hydrangea* are smaller and darker green in color than leaves than plants of 'Horsonn'.
3. Plants of the new *Hydrangea* flower earlier than plants of 'Horsonn'.
4. Inflorescences of plants of the new *Hydrangea* are more high temperature tolerant than inflorescences of plants of 'Horsonn'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Horkron' grown in a container.

The photograph on the second sheet is a close-up view of a typical inflorescence of 'Horkron'.

DETAILED BOTANICAL DESCRIPTION

Plants used in the aforementioned photographs and in the following description were grown in 13-cm containers in a glass-covered greenhouse in Dresden, Germany and under cultural conditions typical of commercial *Hydrangea* production conditions. Plants of the new *Hydrangea* were two years old when the photographs and description were taken. During the production of the plants, day temperatures ranged from 18° C. to 25° C. and night temperatures ranged from 16° C. to 17° C. In the following description, color references are made to The Royal Horticultural Society Colour Chart, 2007 Edition, except where general terms of ordinary dictionary significance are used.

Botanical description: *Hydrangea macrophylla* 'Horkron'.

Parentage:

*Female, or seed, parent*.—Proprietary selection of *Hydrangea macrophylla* identified as code number 13-88/2, not patented.

*Male, or pollen, parent*.—Proprietary selection of *Hydrangea macrophylla* identified as code number 6-97/2, not patented.

Propagation:

*Type cutting*.—By softwood cuttings.

*Time to initiate roots, summer*.—About 15 days at temperatures about 18° C.

*Time to initiate roots, winter*.—About 17 days at temperatures about 18° C.

*Time to produce a rooted young plant, summer*.—About 27 days at temperatures about 18° C.

*Time to produce a rooted young plant, winter*.—About 29 days at temperatures about 18° C.

*Root description*.—Medium in thickness, fibrous; white to grey in color.

*Rooting habit*.—Moderately freely branching; medium density.

Plant description:

*Plant and growth habit*.—Perennial subshrub; compact, upright and mounded plant habit; flattened globular in shape; freely branching habit with about seven lateral branches developing per plant; strong lateral branches; moderately vigorous growth habit.

*Plant height*.—About 24.7 cm.

*Plant diameter or area of spread*.—About 41.6 cm.

*Lateral branches*.—Length: About 15.1 cm. Diameter: About 5.5 mm. Internode length: About 2.7 cm. Texture: Smooth, glabrous. Strength: Strong. Aspect: About 45° from vertical. Color, developing: Close to between 144A and 146D; at the nodes, slightly tinged with close to N186C. Color, developed: Close to 199A to 199C. Lenticels: Density: Dense. Length: About 1.5 mm. Diameter: About 1 mm. Color: Close to N186C.

Leaf description:

*Arrangement*.—Opposite or in whorls of three, simple.

*Length*.—About 11.6 cm.

*Width*.—About 8.6 cm.

*Shape*.—Ovate to oblong.

*Apex*.—Apiculate.

*Base*.—Rounded to short attenuate.

*Margin*.—Serrate.

*Texture, upper surface*.—Glabrous; rugose.

*Texture, lower surface*.—Glabrous; slightly rugose.

*Venation pattern*.—Pinnate.

*Color*.—Developing leaves, upper surface: Darker than between 141A and 143A. Developing leaves, lower surface: Close to 138B. Fully expanded leaves, upper surface: Darker than between N137A and 147A; venation, close to 144A. Fully expanded leaves, lower surface: Close to 147B; venation, close to 144A to 144B.

*Petioles*.—Length: About 2.8 cm. Diameter: About 4 mm. Texture, upper and lower surfaces: Smooth, glabrous. Color, upper and lower surfaces: Close to 144A.

Inflorescence & flower description:

*Flower type and habit*.—Single sterile and inconspicuous fertile flowers arranged on terminal mophead-type panicles; panicles flattened globular in overall shape; fertile flowers face mostly upright and sterile flowers face upright to outwardly.

*Fragrance*.—Faintly fragrant, pleasant.

*Natural flowering season*.—Continuous flowering from late spring to late summer in The Netherlands.

*Flower longevity, fertile flowers*.—Flowers last about one week on the plant; flowers not persistent.

*Flower longevity, sterile flowers*.—Flowers last about six weeks on the plant; flowers persistent.

*Quantity of flowers*.—Freely flowering; about 45 fertile flowers and about 135 sterile flowers per panicle.

*Panicle height*.—About 10.9 cm.

*Panicle diameter*.—About 16.2 cm.

*Flower diameter, fertile flowers*.—About 8 mm.

*Flower depth (height), fertile flowers*.—About 4 mm.

*Flower diameter, sterile flowers*.—About 5 cm.

*Flower depth (height), sterile flowers*.—About 1.4 cm.

*Flower buds, fertile flowers*.—Length: About 3 mm. Diameter: About 4 mm. Shape: Flattened globular. Color: Close to 145C.

*Flower buds, sterile flowers*.—Length: About 8 mm. Diameter: About 7 mm. Shape: Ovoid. Color: Close to 150D; apex, close to 155B.

*Petals, fertile flowers only*.—Quantity and arrangement: Four in a single whorl. Length: About 3 mm. Width: About 2.5 mm. Shape: Broadly ovate, concave. Apex: Acute. Base: Cuneate. Margin: Entire. Texture, upper and lower surfaces: Smooth, glabrous. Color: When opening and fully opened, upper surface: Close to 75B. When opening and fully opened, lower surface: Close to 75C.

*Sepals, fertile flowers*.—Quantity and arrangement: Five in a single whorl. Length: About 1.5 mm. Width: About 1 mm. Shape: Deltoid. Apex: Acute. Base: Broadly cuneate. Margin: Entire. Texture, upper and lower surfaces: Smooth, glabrous. Color, upper and lower surfaces: Close to 75D; apex, close to 145B to 145C.

*Sepals, sterile flowers*.—Quantity and arrangement: Four, occasionally five, in a single whorl. Length: About 2.9 cm. Width: About 3.7 cm. Shape: Reniform. Apex: Rounded to broadly and bluntly acute. Base: Truncate. Margin: Entire to coarsely serrate. Texture, upper and lower surfaces: Smooth, glabrous. Color: When opening, upper surface: Close to 75C; towards the apex, close to 75D. When opening, lower surface: Close to 75C; towards the base, close to 75D. Fully opened, upper surface: Close to 75C to 75D; towards the apex, close to 69D; color does not change with development. Fully opened, lower surface: Close to 75D; towards the apex, close to 69D; color does not change with development.

*Pedicels, fertile flowers*.—Angle: About 20° from vertical. Strength: Moderately strong. Length: About 7 mm. Diameter: About 1 mm. Texture: Smooth, glabrous. Color: Close to 69A and marbled with darker than 63B.

*Pedicels, sterile flowers*.—Angle: About 35° from lateral branch. Strength: Strong. Length: About 2.6 cm. Diameter: About 1.5 mm. Texture: Smooth, glabrous. Color: Close to 69A and marbled with darker than 63B.

*Reproductive organs, fertile flowers only*.—Stamens: Quantity per flower: About eight. Filament length: About 2.5 mm. Filament color: Close to NN155D. Anther length: About 1 mm. Anther shape: Broadly reniform. Anther color: Close to 155D. Pollen amount: Moderate. Pollen color: Close to 155D. Pistils: Pistil quantity per flower: About two. Pistil length: About 1.5 mm. Stigma shape: Club-shaped. Stigma color: Close to NN155A. Style length: About 1 mm. Style color: Close to 155C. Ovary color: Close to 157D.

*Seeds and fruits*.—Seed and fruit development have not been observed on plants of the new *Hydrangea* to date.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Horkron' as illustrated and described.

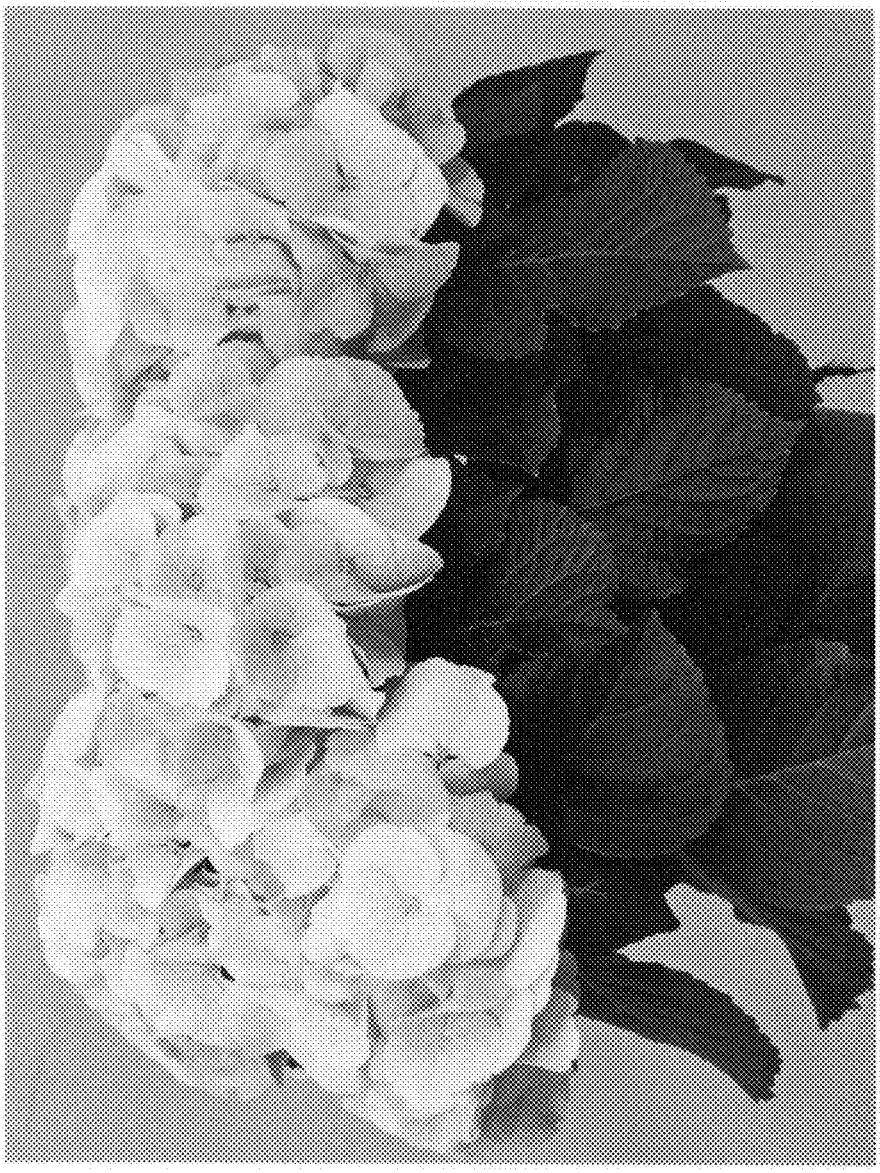

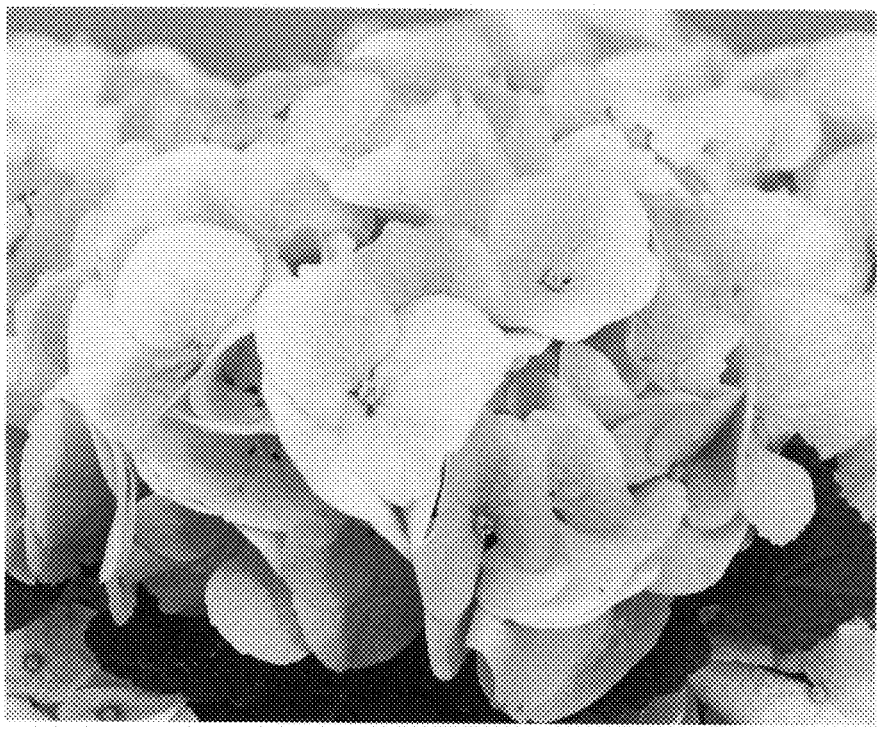

* * * * *